(12) United States Patent
Gaughan (10) Patent No.: US 11,087,863 B2
(45) Date of Patent: Aug. 10, 2021

(54) METHOD AND APPARATUS TO REMOTELY PERFORM MEDICATION RECONCILIATION USING PATIENT MEDICATION RECORDS STORED IN A CLIENT COMPUTING DEVICE

(71) Applicant: Diva Technologies, Inc., Acton, MA (US)

(72) Inventor: Veronica Gaughan, Acton, MA (US)

(73) Assignee: Diva Technologies, Inc., Acton, MA (US)

( * ) Notice: Subject to any disclaimer, the term of this patent is extended or adjusted under 35 U.S.C. 154(b) by 39 days.

(21) Appl. No.: 16/201,507

(22) Filed: Nov. 27, 2018

(65) Prior Publication Data

US 2020/0168309 A1 May 28, 2020

(51) Int. Cl.
*G16H 10/60* (2018.01)
*G16H 10/40* (2018.01)
*G16H 20/10* (2018.01)

(52) U.S. Cl.
CPC ............ *G16H 20/10* (2018.01); *G16H 10/60* (2018.01)

(58) Field of Classification Search
CPC ............ G06F 19/3418; G06F 19/3468; G06F 19/3462; G06F 19/3481; G06F 3/0481; G06F 19/00; G06F 19/3456; G06F 19/328; G06F 19/326; G06F 19/34; G06F 19/325; G06F 21/6245; G16H 10/60; G16H 15/00; G16H 40/20; G16H 20/10; G16H 70/40; G16H 40/60; G16H 40/67; G16H 70/20; G16H 10/20; G16H 40/40; G16H 40/63; G16H 30/20; G16H 50/20; G16H 30/40; G16H 20/40; G06Q 50/24

See application file for complete search history.

(56) References Cited

U.S. PATENT DOCUMENTS

| | | | | |
|---|---|---|---|---|
| 2013/0304512 A1* | 11/2013 | Seshadri | ............... | G06Q 10/00 705/3 |
| 2013/0346104 A1* | 12/2013 | Pillai | ..................... | G16H 10/60 705/3 |
| 2014/0278535 A1* | 9/2014 | Romeo | .................. | G16H 10/60 705/3 |
| 2015/0213204 A1* | 7/2015 | Bose | ...................... | G06F 19/00 705/3 |

* cited by examiner

Primary Examiner — Maroun P Kanaan
(74) Attorney, Agent, or Firm — Compass IP Law, PC (57) ABSTRACT

A system to remotely perform medication reconciliation for a patient in a health care facility using medication records for the patient stored in a client computing device is provided. The system can include the client computing device, servers to securely transfer medication records between the client computing device and a health care facility computer system. The servers, client computing device and a health care facility computer system communicatively coupled via the Internet.

17 Claims, 8 Drawing Sheets

Medicine
Xanax 0.5mg                                                                 600

How to Take
ORAL
602

Instructions
3 Times per day
604

Why prescribed
Anxiety, panic disorder
606

Last Reconciled By
Dr. A
608

Reconciled in
Medical Facility Z
610

Reconciled on
November 1, 2018
612

Date Medication last taken
November 1, 2018
614

Time Medication last taken
1:30p.m.
616

508

| Medicines | Medical Facilities | Side Effects | Notifications |
|---|---|---|---|
| 510 | 512 | 514 | 516 |

METHOD AND APPARATUS TO REMOTELY PERFORM MEDICATION RECONCILIATION USING PATIENT MEDICATION RECORDS STORED IN A CLIENT COMPUTING DEVICE

BACKGROUND

Medication reconciliation is the process to create an accurate list of all medications a patient is taking and to compare the list against the physician's admission, transfer, and/or discharge orders so as to provide correct medications to the patient. The list of medications includes the name, dosage, method of administration, and frequency of the medication. The reconciliation is performed to avoid medication errors such as omissions, duplications, dosing errors, or drug interactions and so that prescribing clinicians have the entire medication profile of the patient before developing a treatment plan and prescribing medications.

When a patient is admitted to a hospital, the patient may not provide an accurate list of medications that includes all the required information including dosage and frequency. In addition, often, the patient does not understand the importance of the accuracy of this information in securing the patient's medical safety. As a result, medication errors result in harming and killing patients every day.

BRIEF DESCRIPTION OF THE DRAWINGS

Features of embodiments of the claimed subject matter will become apparent as the following detailed description proceeds, and upon reference to the drawings, in which like numerals depict like parts, and in which:

Although the following Detailed Description will proceed with reference being made to illustrative embodiments of the claimed subject matter, many alternatives, modifications, and variations thereof will be apparent to those skilled in the art. Accordingly, it is intended that the claimed subject matter be viewed broadly, and be defined only as set forth in the accompanying claims.

DESCRIPTION OF EMBODIMENTS

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

Figure 1:
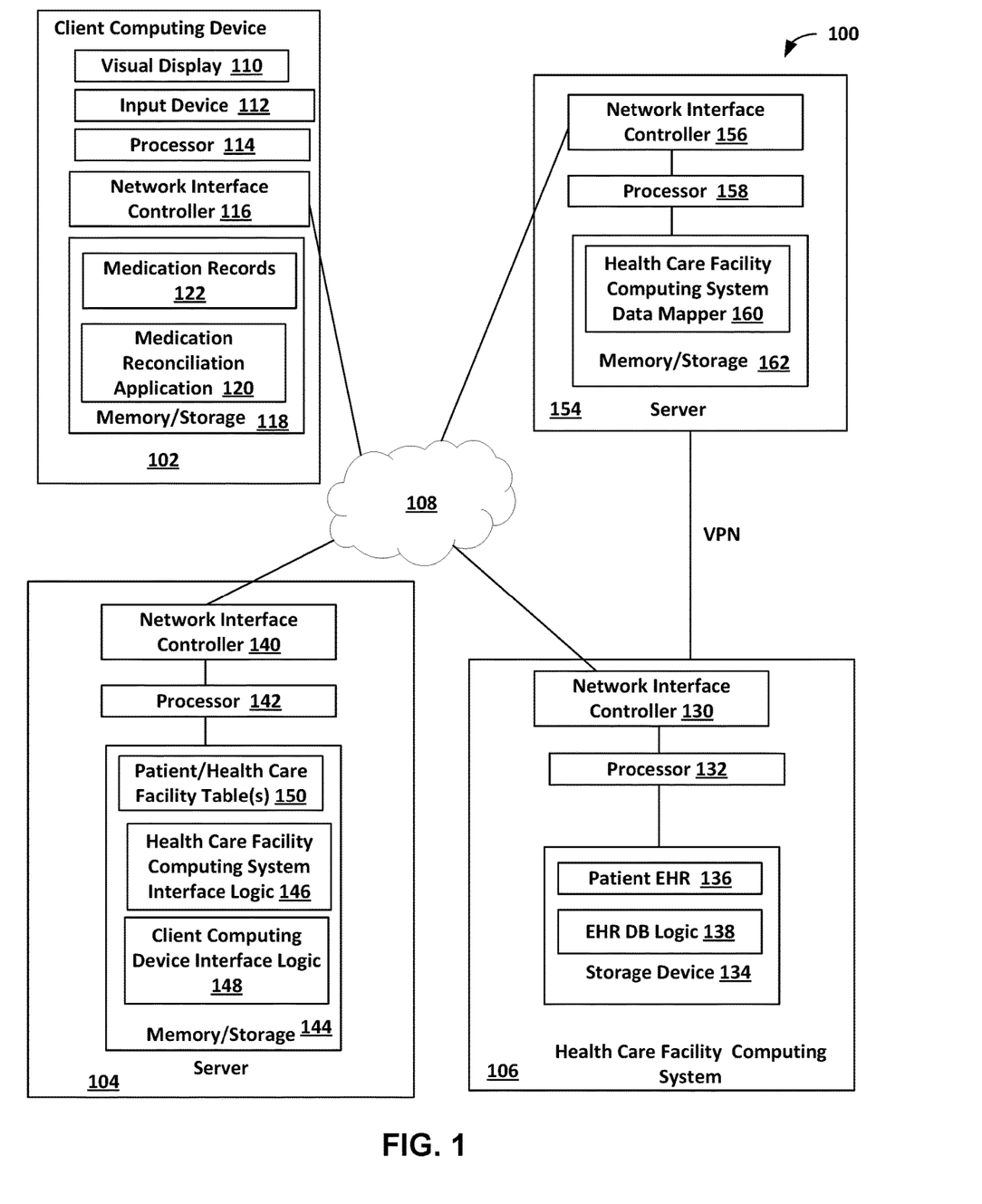
FIG. 1 is a block diagram of a system to remotely perform medication reconciliation using patient medication records stored in a client computing device.

FIG. 1 is a block diagram of a system to remotely perform medication reconciliation using patient medication records stored in a client computing device 102. The system 100 includes the client computing device 102, servers 104, 154, and a health care facility computer system 106 communicatively coupled via a network 108, for example, the Internet.

Examples of health care facilities include a hospital, an urgent care clinic, an ambulatory surgical center and a nursing home. The medication reconciliation is performed by the system 100 for a patient, that is an individual awaiting or under medical care and treatment. The patient can be a user of the client computing device or a person for whom the user of the client computing device is a guardian (for example, a minor child). In an embodiment, computing services (compute, network and storage) provided by the server 104 can be implemented as a virtual machine hosted by a web service provider in a data center.

The client computing device 102 includes a medication reconciliation application 120 to allow a user of the client computing device 102 to view medication records 122 for a patient that are stored in a memory device and/or storage device 118 in the client computing device 102. Examples of client computing devices 102 include a smart phone, a tablet, a personal computer and a smart watch.

The memory device and/or storage device 118 can be persistent or non-volatile memory to store an in-memory database or a storage device such as a hard disk drive or a solid-state drive. The client computing device 102 also includes a processor 114, a display 110 and input device 112. In an embodiment, the input device 112 can be a touchscreen layered on the top of an electronic visual display.

The server 104 includes a network interface controller 140, a processor 142 and a memory device and/or storage device 144. The memory device and/or storage device 144 can be persistent or non-volatile memory to store an in-memory database or a storage device such as a hard disk drive or a solid-state drive.

The Health Care Facility Computing System 106 includes a network controller 130, processor 132 and a storage device 134 to store an Electronic Health Record (EHR) 136 for each patient of the Health Care Facility. An EHR is electronically-stored health information in a digital format. The EHR can include medical history, medication and allergies, immunization status, laboratory test results, radiology images, vital signs, and personal statistics, for example, age and weight. The storage device 134 can be a hard disk drive or a solid-state drive to store EHRs for patients in a database. A patient EHR 136 stored in the EHR database can be accessed by EHR database (DB) logic 138.

The server 154 includes a Health Care Facility Computing System Data Mapper 160, that facilitates healthcare data exchange via a secure Virtual Private Network (VPN), to enable server 154 to communicate with health care facility computing system 106 in a standard way, irrespective of the patient EHR 136 format and the EHR DB logic 138.

The medication reconciliation application 120 in the client computing device 102 can communicate with client computing device 102 interface logic in the server 104 via a network interface controller 140 in the server 104 and the network interface controller 116 in the client computing device 102. The client computing device 102 can receive information downloaded to the server 104 from the health care facility computing system 106 via server 154 and can upload information to the server 104 via the network 108 that can be stored in the server 104 and/or forwarded to the health care facility computing system 106 via server 154. Health care facility computing system interface logic 146 in the server 104 can upload information received from the client computing device 102 to the health care facility computing system 106 via server 154 and forward information received from the health care facility computing system 106 via server 154 to client computing device interface logic 148 to be downloaded to the client computing device 102.

The Health Care Facility Computing System Data Mapper 160 includes logic to convert information received from the client computing device 102 to a format used by the health care facility computing system 106. For example, information can be received from and transmitted to the health care facility computing system 106 using standard JavaScript Object Notation (JSON) format Health Care Facility Computing System Data Mapper 160 converts the information received from the client computing device 102 into a format consistent with Fast Healthcare Interoperability Resources (FHIR), Health Level-7 (HL7), Critical Document Architecture (CDA), or American National Standards Institute (ANSI) Accredited Standards Committee X12 Electronic Data Interchange Extensible Markup Language (XML) standards as implemented by the health care facility computing system 106.

The medication reconciliation application 120 enables a patient to keep track of medication, via a client computing device 102. The patient can communicate medication changes with a health care facility computing system 106 and receive notifications from the health care facility computing system 106. Communication between a registered user on a registered client computing device 102 and a registered medical facility is performed by client computing device interface logic 148, Health Care Facility Computing System Data Mapper 160 and health care facility computing system logic 146. Changes and updates to the patient's health record in a health care facility computing system can be downloaded to the patient's client computing device 102.

Figure 2:
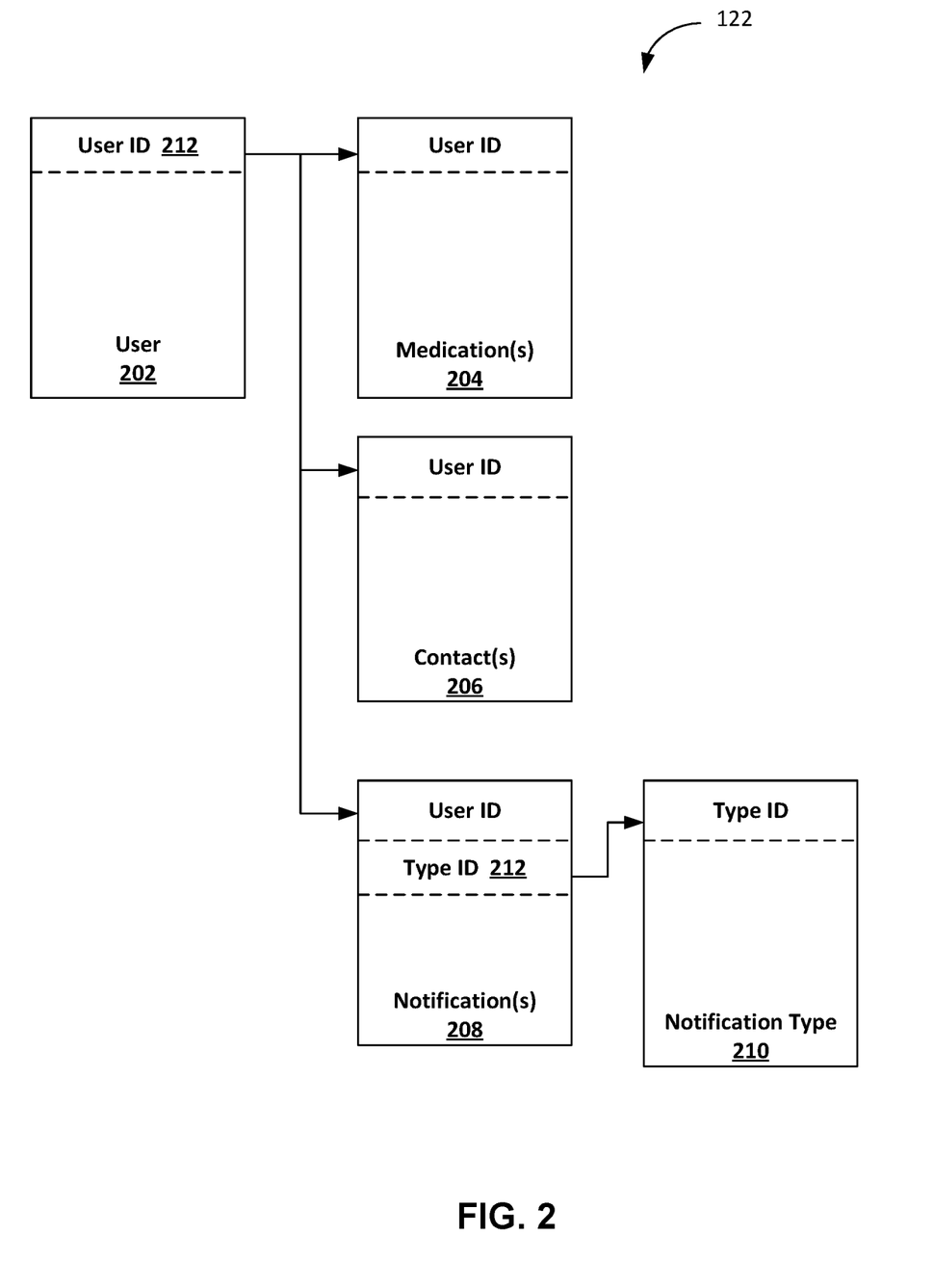
FIG. 2 is a block diagram illustrating organization of medical related information for a patient that is stored in medication records in the memory and/or storage device in the client computing device shown in FIG. 1.

FIG. 2 is a block diagram illustrating organization of medical related information for a patient that is stored in medication records 122 in the memory and/or storage device 118 in the client computing device 102 shown in FIG. 1. A patient who has information stored in medication records 122 in the client computing device 102 is assigned a unique user identifier (ID) that is stored in a user ID entry 212 in a user table 202 associated with the patient. The user identifier is used to link the patient with medical related information, for example, contact(s) 206, medication(s) 204 and notification(s) 208. Each type of notification that can be transferred between the client computing device 102 and the health care facility computing system 106 via server 104 (which may be implemented as a virtual machine as discussed earlier) and server 154 is assigned a Type identifier (ID) 214. Type ID 214 assigned to a notification includes a request to review a medication record, a request to change a medication record, a request to accept shared medications or can be a text message for example: "Your appointment at the Warfarin Clinic is next Tuesday at 10:00 a.m."

Figure 3:
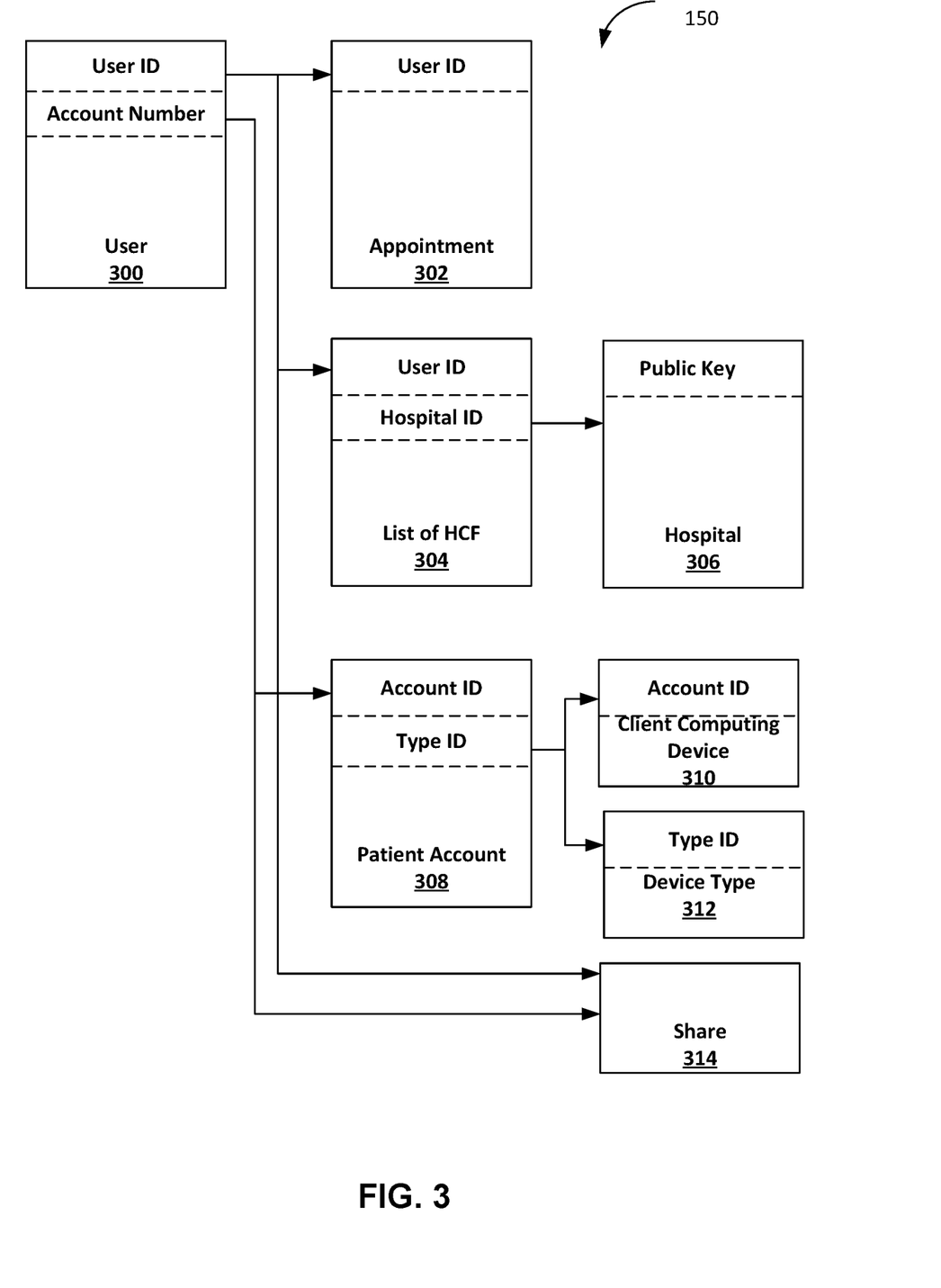
FIG. 3 is a block diagram illustrating patient/health care tables that can be stored in memory and/or storage device in the server shown in FIG. 1.

FIG. 3 is a block diagram illustrating patient/health care tables 150 that can be stored in memory and/or storage device 144 in the server 104 shown in FIG. 1. A table is a systematic arrangement of data usually in rows and columns for ready reference.

A user table 300 can store data related to an account related to a first patient and permissions that the account has to the data for the first patient. For example, permissions can include an indication as to whether medications can be retrieved and/or updated by the account. Permissions can be used in the case where a first patient wants to share data with a second patient's account but doesn't want to give permission to the second patient's account to update medication for the first patent's account. The user table 300 stores limited information about the first patient, for example, only the first patient's name.

A list of hospitals table 304 can include an entry for each hospital (or medical provider) that can be accessed to perform medication reconciliation for a patient. Each hospital (or medical provider) that can be accessed has a unique hospital identifier (or medical provider identifier). The entry can store a location, phone number, and authentication information for the hospital.

A patient account table 308 can include an entry per patient account with each entry in the account table 308 including a patient's name, login information for the patient and links to other users and client computing devices.

A hospital table 306 stores information related to a link between a patient and a hospital. The link between the patient and the hospital is created during an onboarding process with the hospital. During the onboarding process, the link is authenticated to ensure that a patient can only access hospital data relevant to the patient. A list of available hospitals can be generated from the hospital table 306 and downloaded to the client computing device to allow a user to obtain contact information for the hospital and to onboard a hospital.

A device table 310 stores a list of all registered client computing devices 102. Each client computing device 102 is linked to a patient account table 308 and is used to enable sending notifications to the client computing device 102.

Figure 4:
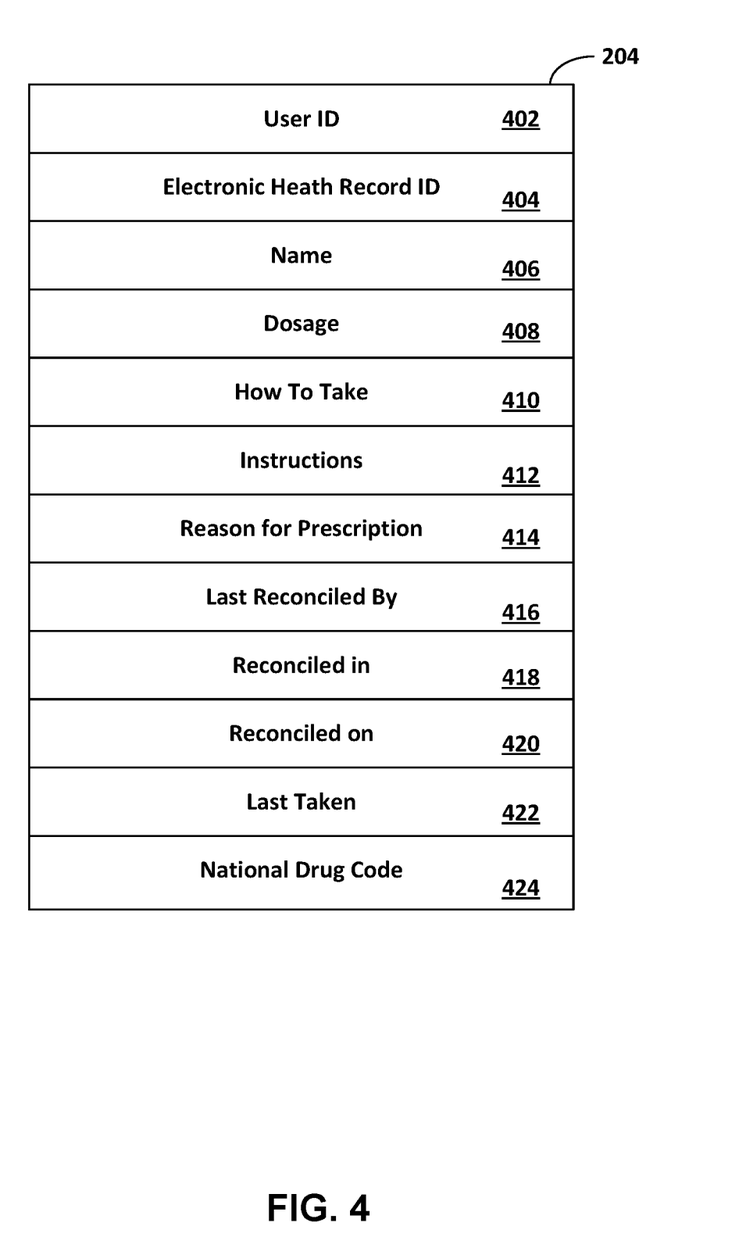
FIG. 4 is a block diagram illustrating the medical related information that can be stored for a medication in medication(s) shown in FIG. 2.

FIG. 4 is a block diagram illustrating the medical related information that can be stored for a medication in medication(s) 204 shown in FIG. 2. Medication(s) 204 table can include a user identifier stored in a user identifier field 402, a patient Electronic Health Record (EHR) identifier assigned to the patient by the health care facility stored in a EHR field 404, a name of a reconciled medication stored in medication name field 406, dosage of the reconciled medication in a dosage field 408, instructions on how to take (route of medication administration) the reconciled medication (for example, oral, otic or subcutaneous), a medical reason for the medication (for example, high blood pressure or diabetes) in a reason for medication field 414, the name of the medical practitioner who last reconciled the medications field 416, the health care facility in which the medication was reconciled (for example, hospital z), reconciliation date (the date that the medication reconciliation was performed) in a reconciled in field 420, the day and time that the medication was last taken by the patient in a last taken field 422, a code assigned to the medication, for example, a National Drug Code in National Drug Code field 424.

National Drug Code (NDC) conforming to the standards set by the U.S. FDA are three-segment numbers which serve as a universal drug product identifier. The segments represent the labeler code, product code and package code. These identify the manufacturer or distributor, the drug product, and the trade package size and type respectively. The NDC digits can appear in the following formats: 4-4-2, 5-3-2 or 5-4-1. The packaging may feature this identifier as a linear barcode or as a 2D data matrix barcode, also known as a Quick Response (QR) code. Drug companies in the U.S. commonly embed the NDC in the GTIN-12 data structure, which consists of 12 digits. The first digit is always 3 and the last one is a control digit which is calculated on the previous 11 digits. The 10 digits in the middle form the NDC. The barcode shown on drug packaging represents the "product identifier" which consists of the NDC GTIN-12, a serial number, a lot number, and an expiration date.

Figure 5:
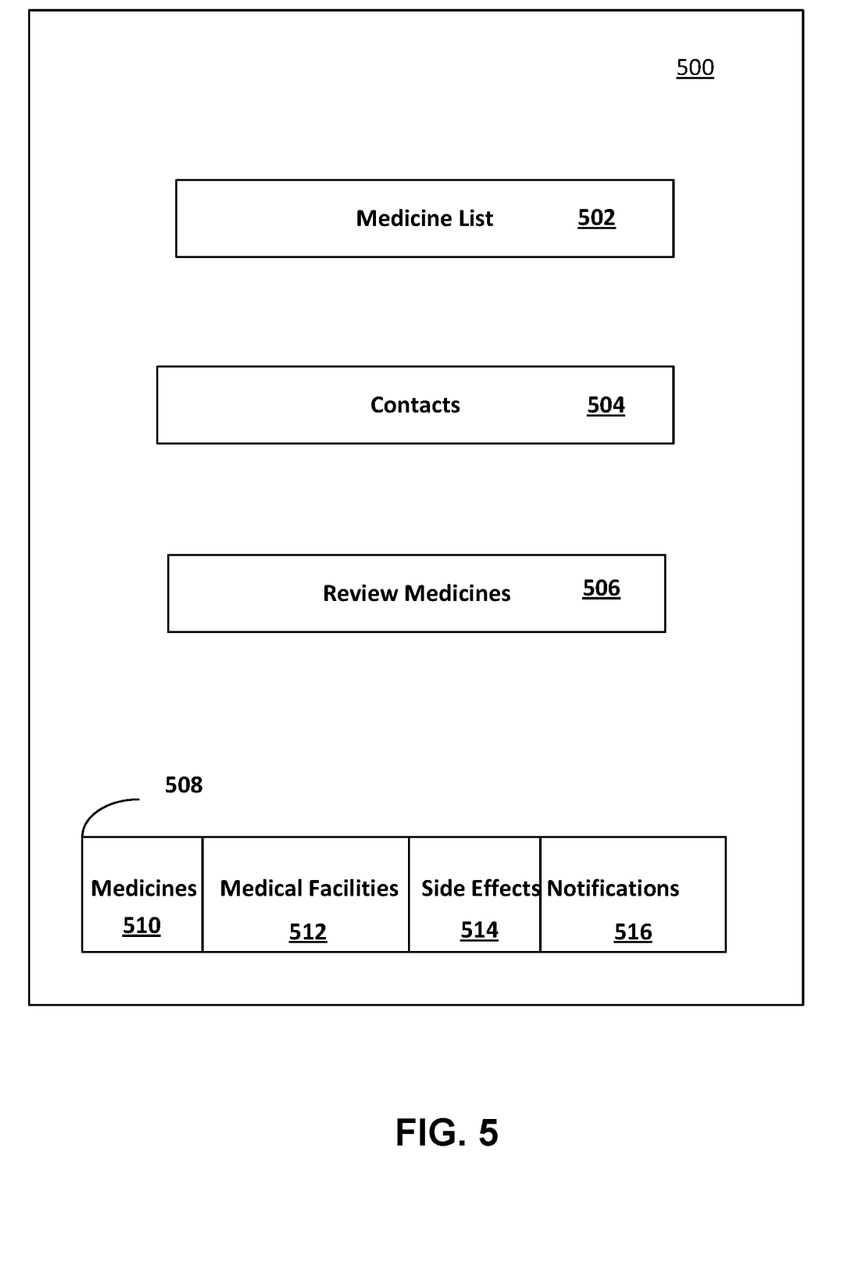
FIG. 5 illustrates a display image stored in memory to be displayed by the display device in the client computing device.

FIG. 5 illustrates a display image 500 stored in memory to be displayed by the display 110 in the client computing device 102. The display image includes selectable buttons that include medicine list 502, contacts 504, review medicines 506, medicines 510, medical facilities 512, side effects 514 and notifications 516.

A medicine list button can be displayed for each user 202. The medicine list for the first user can display the text string "My Medicines." Subsequent medicine list buttons can display a text string that includes the name of the patient, for example, "John's Medicines," "Jane's Medicines." The displayed medicine list for the selected patient can include the most recent list of reconciled medicines for the selected patient including the name, dose and instructions for each medicine for all medicines as reconciled by a clinician at the hospital and any 'over the counter' medicines added manually by the patient.

In an embodiment, medications that have been added manually and have not been shared with the health care facility computing system 106 are displayed separate from medicines that have been verified with the health care facility computing system 106.

When the side effects button 514 is selected known side effects of the medication are displayed on the display 110 in the client computing device 102.

Figure 6:
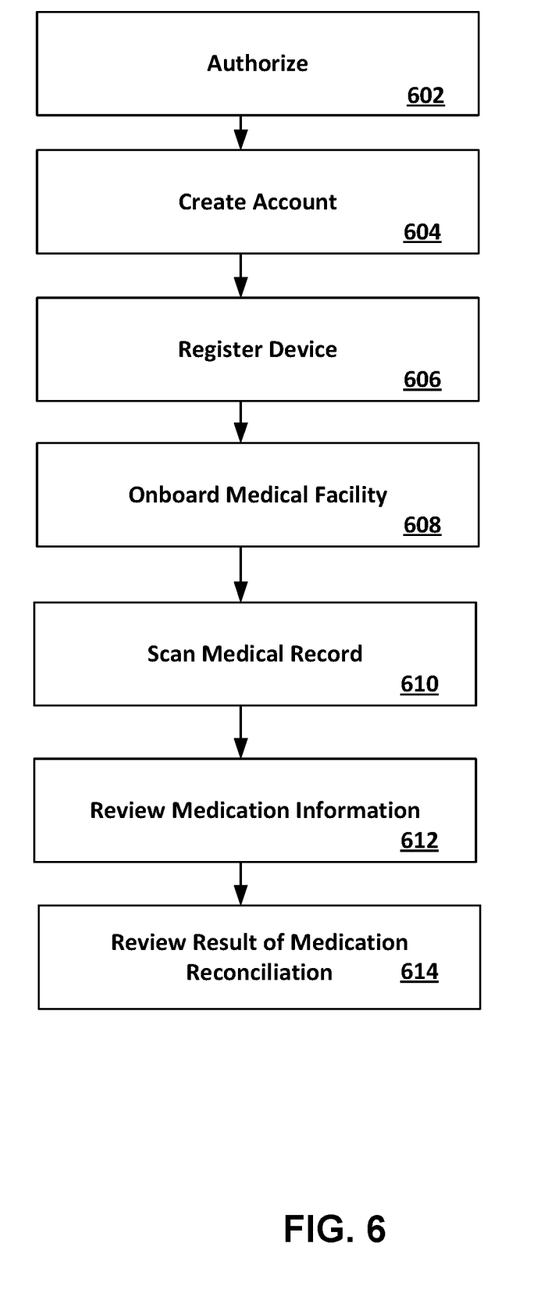
FIG. 6 is a flowgraph illustrating a method for medication reconciliation between a patient and a medical facility that is performed in the health care computing system shown in FIG. 1.

FIG. 6 is a flowgraph illustrating a method for medication reconciliation between a patient and a medical facility that is performed in the health care computing system 100 shown in FIG. 1.

At block 602, in response to a request by a user of the client computing device 102, to start the medication reconciliation application 120 in the client computing device 102, the user is prompted to enter a passcode. If the user enters a valid passcode and the client computing device 102 is connected to the network 108, the passcode is sent to an Authorize Device function in the client computing device interface logic 146 in the server 104. If the passcode is validated, an access token is returned for use in calling other functions in the client computing device interface logic 146 in the server 104.

If the client computing device 102 is not online the user can access functions in the medication reconciliation application that do not require communicating with the server 104 and/or Heath Care Facility Computing System.

At block 604, a user can create an account for patients associated with the client computer device 102. A patient account table 308 is created in the client computing device interface logic 148 per user account. The patient account table 308 stores user information including first name, last name, date of birth, phone number, email address and unique government issued identifier (for example, social security number).

At block 606, the user registers the client computing device 102 with client computing device interface logic 148 in the server 104. In an embodiment, the client computing device is validated by sending a code via text message to the user's telephone number.

At block 608, a user account is linked ("onboarded") to a health care facility computing system. After the user account and health care facility are linked, patient medical data stored in the client computing system and medical data stored in the health care facility computer system can be shared via the server 104 and the server 154

At block 610, the user can be onboarded (authenticating a patient's link to a hospital to establish a link between the user and the hospital so that the user can retrieve and update medication records at the hospital) by scanning a Quick Response (QR) code with a camera in the client computing device 102 and using a QR code reader application on the client computer device 102 to obtain an identifier for the health care facility and user identifier for a patient assigned by the health care facility. A QR code that includes patient identifier, health care facility identifier and is typically printed on documents received associated with a prior visit to the health care facility. If a QR code is not available and/or the camera in the client computing device 102 is not operational, an option is provided to the patient to enter the details manually.

Upon determining that the patient identifier and health care facility identifier in the QR code or those entered manually are valid, the health care facility information and patient identifier are returned to the medication reconciliation application 120 and a link is created between the user and the health care facility in the list of hospitals table 304 for the user. The health care facility information (including telephone number) is stored in the contacts table 206 in the client computer device.

If this is the first health care facility that is on-boarded, then the list of last reconciled medications for the patient can be downloaded from the health care facility and stored in the client computing device 102. If this is the second or subsequent health care facility that is on-boarded, then the list of last reconciled medications, stored in medication(s) 204 table, remains valid and is not changed.

At block 610, if, after onboarding has been completed for a patient and this is the first health care facility on-boarding event and the list of last reconciled medications for the patients has not been already downloaded, a notification can be sent to the client computing device from the heath care facility computing system 106 via the server 104. Upon receipt of the notification, a visible indication that a notification has been received and is waiting to be read is displayed close to the notifications button 516. The notification can indicate that the patient's medicines can be downloaded to the client computing device 102.

At block 612, a user is prompted to start a Medicine Review via "Review Medicines" button 506, which the user can perform at that time or defer to a later time. If medication information for multiple patients is stored on the client computer device 102, the list of patients is displayed on the display 110 to allow the user to select a patient for the medicine review. A new medication can be added by manually adding the details of medication or by scanning a printed barcode affixed to a medication container by a dispensing pharmacy.

Prior to performing a medicine review, a patient is prompted to confirm that the patient has a medical appointment with a medical practitioner (for example, a physician) within a time period (for example, within the next 24 hours). The medical appointment date and time can be stored in an appointment table 302 (FIG. 3).

If the medical appointment is after the time period, any changes that the patient enters are not uploaded to the health care facility computing system and the patient is advised to inform the physician directly as soon as possible. If the patient attempts to carry out a medication review when no medical appointment is scheduled within the time period and the patient records that the patient has ceased to take, or has altered the dose, of a medication that is critical to the patient's health thus putting the patient in a life-threatening situation, the patient might assume that this information has been communicated and thus reviewed by a clinician. However, in the absence of a medical appointment, there is no reason for a clinician to open the patient's EHR and so harm could occur to the patient without the opportunity for a clinician to intervene.

If within the time period, the patient is prompted to review each medication stored in the medication list for the patient. For each medication, the patient can enter via a mediation review form displayed on the display 110 of the client computing device 102. The medication review form allows the patient to indicate if the medication is being taken or no longer being taken. If the mediation is being taken, the patient is prompted to enter the day and time the medication was last taken. If the medication is no longer being taken, the patient is prompted to either choose a reason from a pre-populated of reasons or to enter a reason that the medication is no longer being taken. After the review has been completed, the patient can confirm review is complete, select a health care facility to receive the medication review, confirm medicines to be shared with the health care facility and confirm submission of the updated list. The updated medicine list is transmitted via the network interface controller 116 over the network 108 to the client computing device interface logic 148 in the server 104 and the server 154 to be uploaded to the health care facility computing system 106.

At block 614, after a clinician has performed medication reconciliation using the medication review received from the patient and a consultation with the patient, medication reconciliation is carried out in the health care facility and the updated list of reconciled medication information is transmitted to the client computing device 102 over the network 108 via the server 154 and the server 104 and can be displayed on the display 110 in the client computing device 102.

Figure 7:
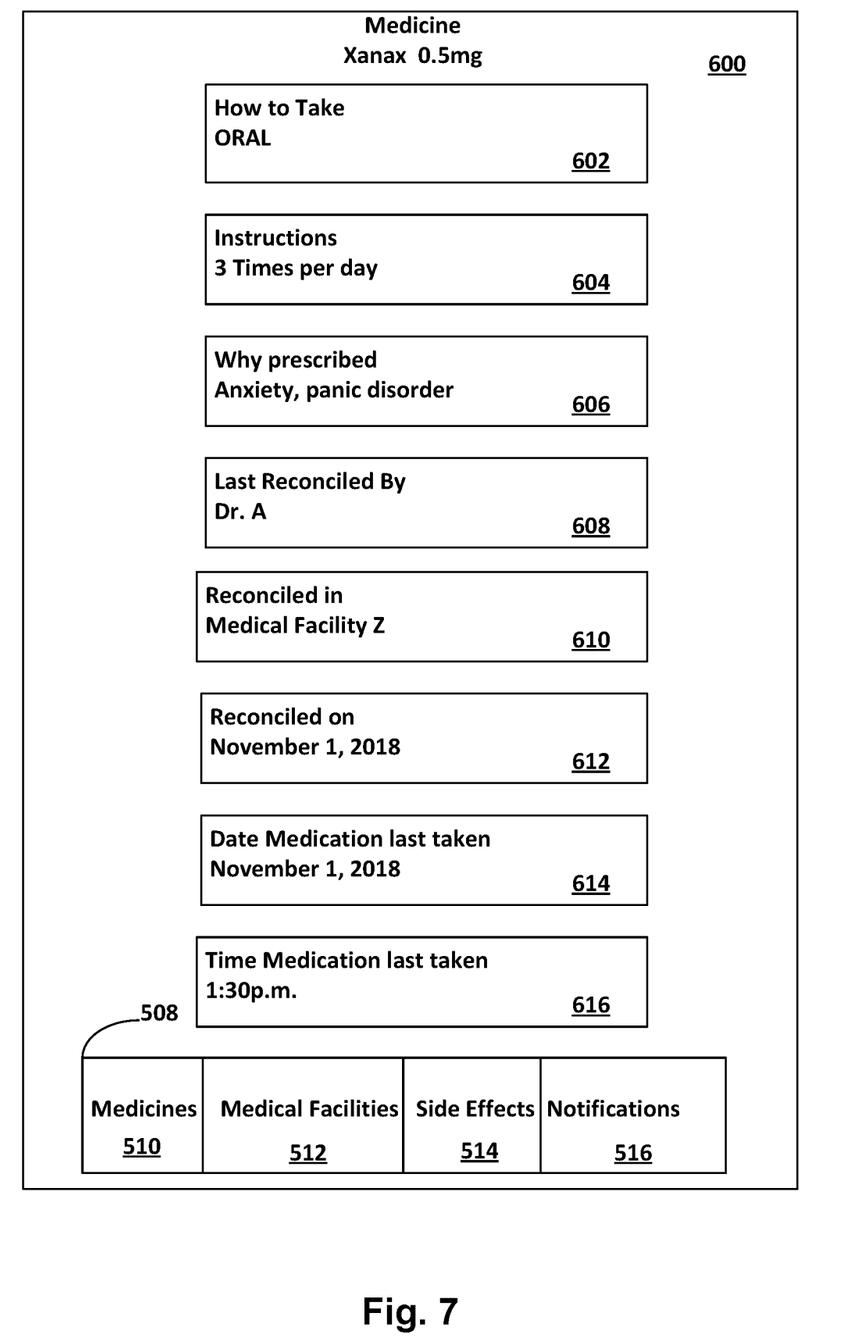
FIG. 7 illustrates a display image of the result of medication reconciliation performed by a clinician in the health care facility computing system stored in memory/storage in the client computing device.

FIG. 7 illustrates a display image of the result of medication reconciliation performed by a clinician in the health care facility computing system 106 stored in memory/storage 118 in the client computing device 102.

In the example shown in FIG. 7, the medication is Xanax and the dose is 0.5 mg. The patient medication information stored in medication(s) 204 table (FIG. 4) and sent to the health care facility computing system 106 shown in FIG. 4 is displayed in fields 702, 704, 706, 714 and 716. Fields 708, 710 and 712 include the reconciliation clinician, medical facility and date respectively completed by a clinician at the medical facility.

Figure 8:
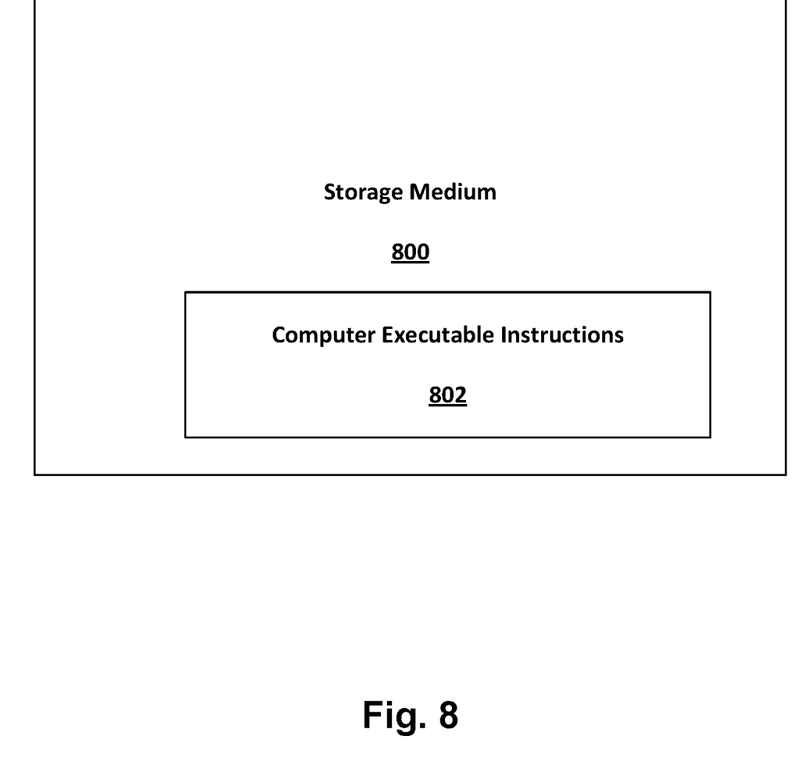
FIG. 8 illustrates an example of a storage medium.

FIG. 8 illustrates an example of a storage medium 800. Storage medium 800 may comprise an article of manufacture. In some examples, storage medium 800 may include any non-transitory computer readable medium or machine readable medium, such as an optical, magnetic or semiconductor storage. Storage medium 800 may store various types of computer executable instructions, such as instructions 802 to implement logic flows of FIG. 6, respectively. Examples of a computer readable or readable storage medium may include any tangible media or tangible machine readable-medium capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The examples are not limited in this context.

Flow diagrams as illustrated herein provide examples of sequences of various process actions. The flow diagrams can indicate operations to be executed by a software or firmware routine, as well as physical operations. In one embodiment, a flow diagram can illustrate the state of a finite state machine (FSM), which can be implemented in hardware and/or software. Although shown in a particular sequence or order, unless otherwise specified, the order of the actions can be modified. Thus, the illustrated embodiments should be understood only as an example, and the process can be performed in a different order, and some actions can be performed in parallel. Additionally, one or more actions can be omitted in various embodiments; thus, not all actions are required in every embodiment. Other process flows are possible.

To the extent various operations or functions are described herein, they can be described or defined as software code, instructions, configuration, and/or data. The content can be directly executable ("object" or "executable" form), source code, or difference code ("delta" or "patch" code). The software content of the embodiments described herein can be provided via an article of manufacture with the content stored thereon, or via a method of operating a communication interface to send data via the communication interface. A machine readable storage medium can cause a machine to perform the functions or operations described, and includes any mechanism that stores information in a form accessible by a machine (e.g., computing device, electronic system, etc.), such as recordable/non-recordable media (e.g., read only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface can be configured by providing configuration parameters and/or sending signals to prepare the communication interface to provide a data signal describing the software content. The communication interface can be accessed via one or more commands or signals sent to the communication interface.

Various components described herein can be a means for performing the operations or functions described. Each component described herein includes software, hardware, or a combination of these. The components can be implemented as software modules, hardware modules, special-purpose hardware (e.g., application specific hardware, application specific integrated circuits (ASICs), digital signal processors (DSPs), etc.), embedded controllers, hardwired circuitry, etc.

Besides what is described herein, various modifications can be made to the disclosed embodiments and implementations of the invention without departing from their scope.

What is claimed is:

1. An apparatus comprising:
   a storage device to store a medication record associated with a patient identifier, the medication record including at least one health care facility associated with the patient identifier and a date and a time of a medical appointment at a health care facility;
   a network interface to receive medication information stored on a patient's client computing device, the medication information including the patient identifier, a medical provider identifier associated with the patient identifier and medication information associated with the patient identifier;
   a health care facility computing system data mapper comprising logic to convert medication information received from the patient's client computing device to a format used by a health care facility computing system; and
   health care facility computing system interface logic to enable upload of received medication information within a time period prior to the date and time of the medical appointment, the network interface to transmit the converted received medication information over a network to the health care facility computing system if upload of the converted received medication information is enabled, and to transmit reconciled medication information for the patient identifier received from the health care facility computing system to the patient's client computing device.

2. The apparatus of claim 1, wherein the patient's client computing device is a smart phone.

3. The apparatus of claim 1, wherein the health care facility is a hospital.

4. The apparatus of claim 1, wherein the reconciled medication information includes a reconciliation date, a name of the health care facility, medication reconciliation and a name of a clinician that performed the medication reconciliation.

5. The apparatus of claim 1, wherein the medication information includes a medication name, a dosage for the medication name, a reason for the medication name, and an Electronic Health Record identifier assigned by the health care facility to the patient identifier.

6. The apparatus of claim 5, wherein the medication information includes a route to take a medication.

7. The apparatus of claim 1, wherein the storage device to store an account for the patient identifier, the account associated with the patient's client computing device.

8. A method comprising:
   storing, in a storage device, a medication record associated with a patient identifier, the medication record including at least one health care facility associated with the patient identifier and a date and a time of a medical appointment at a health care facility;
   receiving via a network interface, medication information stored on a patient's client computing device, the medication information including the patient identifier, a medical provider identifier associated with the patient identifier and medication information associated with the patient identifier;
   converting, by a health care facility computing system data mapper, medication information received from the patient's client computing device to a format used by the health care facility computing system;
   transmitting, via the network interface, the converted received medication information over a network to a health care facility computing system if upload of the received medication information is enabled by health care facility computing system interface logic within a time period prior to the date and time of the medical appointment; and
   transmitting reconciled medication information for the patient identifier received from the health care facility computing system to the patient's client computing device.

9. The method of claim 8, wherein the reconciled medication information includes a reconciliation date, a name of the health care facility, medication reconciliation and a name of a clinician that performed the medication reconciliation.

10. The method of claim 8, wherein the medication information includes a medication name, a dosage for the medication name, a reason for the medication name, and an Electronic Health Record identifier assigned by the health care facility to the patient identifier.

11. The method of claim 10, wherein the medication information includes a route to take a medication.

12. The method of claim 8, wherein the storage device to store an account for the patient identifier, the account associated with the patient's client computing device.

13. At least one tangible machine-readable medium comprising a plurality of instructions that in response to being executed by a processor cause the processor to:
   store, in a storage device, a medication record associated with a patient identifier, the medication record including at least one health care facility associated with the patient identifier and a date and a time of a medical appointment at a health care facility;
   receive via a network interface, medication information stored on a patient's client computing device, the medication information including the patient identifier, a medical provider identifier associated with the patient identifier and medication information associated with the patient identifier;
   convert, by a health care facility computing system data mapper, the medication information received from the patient's client computing device to a format used by a health care facility computing system;
   transmit, via the network interface, the converted received medication information over a network to a health care facility computing system if upload of received medication information is enabled by health care facility computing system interface logic within a time period prior to the date and time of the medical appointment; and
   transmit reconciled medication information for the patient identifier received from the health care facility computing system to the patient's client computing device.

14. The tangible machine-readable medium of claim 13, wherein the reconciled medication information includes a reconciliation date, a name of the health care facility, medication reconciliation and a name of a clinician that performed the medication reconciliation.

15. The tangible machine-readable medium of claim 13, wherein the medication information includes a medication name, a dosage for the medication name, a reason for the medication name, and an Electronic Health Record identifier assigned by the health care facility to the patient identifier.

16. The tangible machine-readable medium of claim 13, wherein the medication information includes a route to take a medication.

17. The tangible machine-readable medium of claim 13, comprising instructions to store an account for the patient identifier, the account associated with the patient's client computing device.

\* \* \* \* \*